US007070783B1

(12) United States Patent
Chernajovsky et al.

(10) Patent No.: US 7,070,783 B1
(45) Date of Patent: Jul. 4, 2006

(54) SMALL MOLECULAR WEIGHT TNF RECEPTOR MULTIMERIC MOLECULE

(75) Inventors: Yuti Chernajovsky, London (GB); Richard Neve, Sandwich (GB); Marc Feldmann, London (GB)

(73) Assignee: The Mathilda and Terence Kennedy Institute of Rheumatology, London (GB)

( * ) Notice: Subject to any disclaimer, the term of this patent is extended or adjusted under 35 U.S.C. 154(b) by 0 days.

(21) Appl. No.: 09/285,531

(22) Filed: Apr. 2, 1999

Related U.S. Application Data (63) Continuation of application No. 08/437,533, filed on May 9, 1995, now abandoned.

(51) Int. Cl.
*A61K 38/17* (2006.01)
*C07K 14/705* (2006.01)
*C07H 21/04* (2006.01)

(52) U.S. Cl. .............................. 424/185.1; 424/192.1; 514/12; 530/350; 536/23.4; 536/23.5

(58) Field of Classification Search ................ 530/350; 514/2; 435/69.2
See application file for complete search history.

(56) References Cited

U.S. PATENT DOCUMENTS

| | | | |
|---|---|---|---|
| 5,395,760 A | 3/1995 | Smith et al. | |
| 5,447,851 A | 9/1995 | Beutler et al. | ............. 435/69.7 |
| 5,470,952 A | 11/1995 | Stahl et al. | |
| 5,478,925 A | 12/1995 | Wallach et al. | |
| 5,610,279 A | 3/1997 | Brockhaus et al. | ....... 530/387.3 |
| 5,721,121 A | 2/1998 | Etcheverry et al. | ........ 435/69.7 |
| 5,736,387 A * | 4/1998 | Paul et al. | ............... 435/320.1 |
| 5,945,397 A | 8/1999 | Smith et al. | ................... 514/2 |
| 5,958,409 A | 9/1999 | Turk et al. | ............... 424/141.1 |
| 6,015,557 A | 1/2000 | Tobinick et al. | ......... 424/134.1 |
| RE36,755 E | 6/2000 | Smith et al. | ............... 435/69.1 |

FOREIGN PATENT DOCUMENTS

| | | |
|---|---|---|
| EP | 526 905 A2 | 2/1993 |
| WO | WO 92/07076 | 4/1992 |
| WO | WO 95 03827 | 2/1995 |
| WO | WO 98/05357 | 2/1998 |
| WO | WO 00/59530 | 10/2000 |

OTHER PUBLICATIONS

Lesslauer, W., et al., "Recombinant soluble tumor necrosis factor receptor proteins protect mice from lipopolysaccharide-induced lethality", *Eur. J. Immunol*, 21:2883-2886 (1991).

Baker, D., et al., "Control of established experimental allergic encephalomyelitis by inhibition of tumor necrosis factor (TNF) activity within the central nervous system using monoclonal antibodies and TNF receptor-immunoglobulin fusion proteins", *Eur. J. Immunol.*, 24:2040-2048 (1994).

Corocoran, A.E., et al., "Characterization of ligand binding by the human p55 tumour-necrosis-factor receptor", *Eur. J. Biochem.*, 223:831-840 (1994).

Kim, C.-D. and Bloedow, D.C., "Administration Route Dependency of Distribution of PEGylated Recombinant HumanTumor Necrosis Factor Binding Protein (rhTNFbp-PEG20K dimer) Following i.v. and s.c. Injection in Rats", *Arch. Pharm. Res.*, 17(5) :381-382 (1994).

Kolls, J. et at., "Prolonged and effective blockade of tumor necrosis factor activity through adenovirus-mediated gene transfer", *Proc. Natl. Acad. Sci. USA*, 91:215-219 (1994).

Elliott, M.J., et al., "Treatment of rheumatoid arthritis with chimeric monoclonal antibodies to tumor necrosis factor α", *Arthritis & Rheumatism*, 36(12)1681-1690 (1993).

Butler, D.M., et al., "TNF receptor fusion proteins are effective inhibitors of TNF-mediated cytotoxicity on human KYM-1D4 rhabdomyosarcoma cells", *Cytokine,*6(6) :616-623 (1994).

Bemelmans, M.H.A., et al., "Tissue distribution and clearance of soluble murine TNF receptors in mice", *Cytokine*, 6(6) :608-615 (1994).

Neve, R., et al., "Expression of an Efficient Small Molecular Weight Tumour Necrosis Factor/Lymphotoxin Antagonist," *Cytokine 8*(5) : 365-370 (May 1996).

* cited by examiner

*Primary Examiner*—Eileen B. O'Hara
(74) *Attorney, Agent, or Firm*—John P. White, Esq.; Cooper & Dunham LLP (57) ABSTRACT

The present invention relates to a receptor molecule which binds to TNF comprising all or a functional portion of the extracellular domain (ECD) of two or more TNF-Rs linked via one or more polypeptide linkers. The receptor can further comprise a signal peptide of a secreted protein, such as the signal peptide of the extracellular domain of the TNF-R or the signal peptide of a cytokine. The invention also relates to isolated DNA encoding a receptor molecule which binds to TNF, comprising two or more sequences encoding all or a functional portion of the ECD of TNF-Rs linked via one or more sequences encoding a polypeptide linker. The invention further relates to a method of making a construct which expresses all or a functional portion of the ECD of two or more TNF-Rs linked via one or more polypeptide linkers and cells which express the construct. The invention also relates to a method of inhibiting the biological activity of TNF in a host comprising administering to the host an effective amount of a receptor molecule of the present invention. The invention further relates to receptor molecules which bind cytokines that bind to receptor molecules comprising more than one subunit.

10 Claims, 5 Drawing Sheets

FIG. 1

CLONING OF Hu p75 TNF-R ECD dimer INTO THE RETROVIRAL VECTOR pBabeNeo.

FIG. 2

TNF-R dimer OSCAR Sequence

```
          10              20              30              40              50              60
123 456 789 012 345 678 901 234 567 890 123 456 789 012 345 678 901 234 567 890
ATG GCG CCC GTC GCC GTC TGG GCC GCG CTG GCC GTC GGA CTG GAG CTC TGG GCT GCG GCC      60
 M   A   P   V   A   V   W   A   A   L   A   V   G   L   E   L   W   A   A   A
CAC GCC TTG CCC GCC CAG GTG GCA TTT ACA CCC TAC GCC CCG GAG CCC GGG AGC ACA TGC     120
 H   A   L   P   A   Q   V   A   F   T   P   Y   A   P   E   P   G   S   T   C
CGG CTC AGA GAA TAC TAT GAC CAG ACA GCT CAG ATG TGC TGC AGC AAA TGC TCG CCG GGC     180
 R   L   R   E   Y   Y   D   Q   T   A   Q   M   C   C   S   K   C   S   P   G
CAA CAT GCA AAA GTC TTC TGT ACC AAG ACC TCG GAC ACC GTG TGT GAC TCC TGT GAG GAC     240
 Q   H   A   K   V   F   C   T   K   T   S   D   T   V   C   D   S   C   E   D
AGC ACA TAC ACC CAG CTC TGG AAC TGG GTT CCC GAG TGC TTG AGC TGT GGC TCC CGC TGT     300
 S   T   Y   T   Q   L   W   N   W   V   P   E   C   L   S   C   G   S   R   C
AGC TCT GAC CAG GTG GAA ACT CAA GCC TGC ACT CGG GAA CAG AAC CGC ATC TGC ACC TGC     360
 S   S   D   Q   V   E   T   Q   A   C   T   R   E   Q   N   R   I   C   T   C
AGG CCC GGC TGG TAC TGC GCG CTG AGC AAG CAG GAG GGG TGC CGG CTG TGC GCG CCG CTG     420
 R   P   G   W   Y   C   A   L   S   K   Q   E   G   C   R   L   C   A   P   L
CGC AAG TGC CGC CCG GGC TTC GGC GTG GCC AGA CCA GGA ACT GAA ACA TCA GAC GTG GTG     480
 R   K   C   R   P   G   F   G   V   A   R   P   G   T   E   T   S   D   V   V
TGC AAG CCC TGT GCC CCG GGG ACG TTC TCC AAC ACG ACT TCA TCC ACG GAT ATT TGC AGG     540
 C   K   P   C   A   P   G   T   F   S   N   T   T   S   S   T   D   I   C   R
CCC CAC CAG ATC TGT AAC GTG GTG GCC ATC CCT GGG AAT GCA AGC ATG GAT GCA GTC TGC     600
 P   H   Q   I   C   N   V   V   A   I   P   G   N   A   S   M   D   A   V   C
ACG TCC ACG TCC CCC ACC CGG AGT ATG GCC CCA GGG GCA GTA CAC TTA CCC CAG CCA GTG     660
 T   S   T   S   P   T   R   S   M   A   P   G   A   V   H   L   P   Q   P   V
TCC ACA CGA TCC CAA CAC ACG CAG CCA ACT CCA GAA CCC AGC ACC TCT TCC TGC TCC TCC     720
 S   T   R   S   Q   H   T   Q   P   T   P   E   P   S   T   S   S   C   S   S
TTC CTG CTC CCA ATG GGC CCC AGC CCC CAG GCT AGA GGT GGG GGT TCT GGC GGC GGC         780
 F   L   L   P   M   G   P   S   P   Q   A   R   G   G   G   S   G   G   G
GGT TCG GGC GGC GGT GGC TCG GAT CCC GCC CAG GTG GCA TTT ACA CCC TAC GCC CCG GAG     840
 G   S   G   G   G   G   S   D   P   A   Q   V   A   F   T   P   Y   A   P   E
CCC GGG AGC ACA TGC CGG CTC AGA GAA TAC TAT GAC CAG ACA GCT CAG ATG TGC TGC AGC     900
 P   G   S   T   C   R   L   R   E   Y   Y   D   Q   T   A   Q   M   C   C   S
AAA TGC TCG CCG GGC CAA CAT GCA AAA GTC TTC TGT ACC AAG ACC TCG GAC ACC GTG TGT     960
 K   C   S   P   G   Q   H   A   K   V   F   C   T   K   T   S   D   T   V   C
GAC TCC TGT GAG GAC AGC ACA TAC ACC CAG CTC TGG AAC TGG GTT CCC GAG TGC TTG AGC    1020
 D   S   C   E   D   S   T   Y   T   Q   L   W   N   W   V   P   E   C   L   S
TGT GGC TCC CGC TGT AGC TCT GAC CAG GTG GAA ACT CAA GCC TGC ACT CGG GAA CAG AAC    1080
 C   G   S   R   C   S   S   D   Q   V   E   T   Q   A   C   T   R   E   Q   N
CGC ATC TGC ACC TGC AGG CCC GGC TGG TAC TGC GCG CTG AGC AAG CAG GAG GGG TGC CGG    1140
 R   I   C   T   C   R   P   G   W   Y   C   A   L   S   K   Q   E   G   C   R
CTG TGC GCG CCG CTG CGC AAG CGC CCG GGC TTC GGC GTG GCC AGA CCA GGA ACT GAA        1200
 L   C   A   P   L   R   K   C   R   P   G   F   G   V   A   R   P   G   T   E
ACA TCA GAC GTG GTG TGC AAG CCC TGT GCC CCG GGG ACG TTC TCC AAC ACG ACT TCA TCC    1260
 T   S   D   V   V   C   K   P   C   A   P   G   T   F   S   N   T   T   S   S
ACG GAT ATT TGC AGG CCC CAC CAG ATC TGT AAC GTG GTG GCC ATC CCT GGG AAT GCA AGC    1320
 T   D   I   C   R   P   H   Q   I   C   N   V   V   A   I   P   G   N   A   S
ATG GAT GCA GTC TGC ACG TCC ACG TCC CCC ACC CGG AGT ATG GCC CCA GGG GCA GTA CAC    1380
 M   D   A   V   C   T   S   T   S   P   T   R   S   M   A   P   G   A   V   H
TTA CCC CAG CCA GTG TCC ACA CGA TCC CAA CAC ACG CAG CCA ACT CCA GAA CCC AGC ACT    1440
 L   P   Q   P   V   S   T   R   S   Q   H   T   Q   P   T   P   E   P   S   T
GCT CCA AGC ACC TCC TTC CTG CTC CCA ATG GGC CCC AGC CCC CCA GCT GAA GGG AGC ACT    1500
 A   P   S   T   S   F   L   L   P   M   G   P   S   P   P   A   E   G   S   T
GGC TAG                                                                            1506
 G
```

FIG. 5A TNF standard curve

FIG. 5B Hu TNF-R-ECD monomer

FIG. 5C p75 sf2

FIG. 5D Hu TNF-R ECD dimer

SEQUENCE LISTING

```
<160> NUMBER OF SEQ ID NOS: 4

<210> SEQ ID NO 1
<211> LENGTH: 1506
<212> TYPE: DNA
<213> ORGANISM: Artificial Sequence
<220> FEATURE:
<221> NAME/KEY: CDS
<222> LOCATION: (1)...(1506)
<223> OTHER INFORMATION: Open Reading Frame of Human P75 TNF-R ECD

<400> SEQUENCE: 1 atg gcg ccc gtc gcc gtc tgg gcc gcg ctg gcc gtc gga ctg gag ctc       48
Met Ala Pro Val Ala Val Trp Ala Ala Leu Ala Val Gly Leu Glu Leu
 1               5                  10                  15 tgg gct gcg gcg cac gcc ttg ccc gcc cag gtg gca ttt aca ccc tac       96
Trp Ala Ala Ala His Ala Leu Pro Ala Gln Val Ala Phe Thr Pro Tyr
             20                  25                  30 gcc ccg gag ccc ggg agc aca tgc cgg ctc aga gaa tac tat gac cag      144
Ala Pro Glu Pro Gly Ser Thr Cys Arg Leu Arg Glu Tyr Tyr Asp Gln
         35                  40                  45 aca gct cag atg tgc tgc agc aaa tgc tcg ccg ggc caa cat gca aaa      192
Thr Ala Gln Met Cys Cys Ser Lys Cys Ser Pro Gly Gln His Ala Lys
     50                  55                  60 gtc ttc tgt acc aag acc tcg gac acc gtg tgt gac tcc tgt gag gac      240
Val Phe Cys Thr Lys Thr Ser Asp Thr Val Cys Asp Ser Cys Glu Asp
 65                  70                  75                  80 agc aca tac acc cag ctc tgg aac tgg gtt ccc gag tgc ttg agc tgt      288
Ser Thr Tyr Thr Gln Leu Trp Asn Trp Val Pro Glu Cys Leu Ser Cys
                 85                  90                  95 ggc tcc cgc tgt agc tct gac cag gtg gaa act caa gcc tgc act cgg      336
Gly Ser Arg Cys Ser Ser Asp Gln Val Glu Thr Gln Ala Cys Thr Arg
            100                 105                 110 gaa cag aac cgc atc tgc acc tgc agg ccc ggc tgg tac tgc gcg ctg      384
Glu Gln Asn Arg Ile Cys Thr Cys Arg Pro Gly Trp Tyr Cys Ala Leu
        115                 120                 125
```

-continued

| | |
|---|---|
| agc aag cag gag ggg tgc cgg ctg tgc gcg ccg ctg cgc aag tgc cgc<br>Ser Lys Gln Glu Gly Cys Arg Leu Cys Ala Pro Leu Arg Lys Cys Arg<br>130                       135                   140 | 432 |
| ccg ggc ttc ggc gtg gcc aga cca gga act gaa aca tca gac gtg gtg<br>Pro Gly Phe Gly Val Ala Arg Pro Gly Thr Glu Thr Ser Asp Val Val<br>145                       150                   155                   160 | 480 |
| tgc aag ccc tgt gcc ccg ggg acg ttc tcc aac acg act tca tcc acg<br>Cys Lys Pro Cys Ala Pro Gly Thr Phe Ser Asn Thr Thr Ser Ser Thr<br>                   165                   170                   175 | 528 |
| gat att tgc agg ccc cac cag atc tgt aac gtg gtg gcc atc cct ggg<br>Asp Ile Cys Arg Pro His Gln Ile Cys Asn Val Val Ala Ile Pro Gly<br>             180                   185                   190 | 576 |
| aat gca agc atg gat gca gtc tgc acg tcc acg tcc ccc acc cgg agt<br>Asn Ala Ser Met Asp Ala Val Cys Thr Ser Thr Ser Pro Thr Arg Ser<br>         195                   200                   205 | 624 |
| atg gcc cca ggg gca gta cac tta ccc cag cca gtg tcc aca cga tcc<br>Met Ala Pro Gly Ala Val His Leu Pro Gln Pro Val Ser Thr Arg Ser<br>210                       215                   220 | 672 |
| caa cac acg cag cca act cca gaa ccc agc act gct cca agc acc tcc<br>Gln His Thr Gln Pro Thr Pro Glu Pro Ser Thr Ala Pro Ser Thr Ser<br>225                       230                   235                   240 | 720 |
| ttc ctg ctc cca atg ggc ccc agc ccc cca gct aga ggt ggg ggc ggt<br>Phe Leu Leu Pro Met Gly Pro Ser Pro Pro Ala Arg Gly Gly Gly Gly<br>                   245                   250                   255 | 768 |
| tcg ggt ggc ggc ggc tcg ggc ggg ggt ggc tcg gat ccc gcc cag gtg<br>Ser Gly Gly Gly Gly Ser Gly Gly Gly Gly Ser Asp Pro Ala Gln Val<br>             260                   265                   270 | 816 |
| gca ttt aca ccc tac gcc ccg gag ccc ggg agc aca tgc cgg ctc aga<br>Ala Phe Thr Pro Tyr Ala Pro Glu Pro Gly Ser Thr Cys Arg Leu Arg<br>         275                   280                   285 | 864 |
| gaa tac tat gac cag aca gct cag atg tgc tgc agc aaa tgc tcg ccg<br>Glu Tyr Tyr Asp Gln Thr Ala Gln Met Cys Cys Ser Lys Cys Ser Pro<br>290                       295                   300 | 912 |
| ggc caa cat gca aaa gtc ttc tgt acc aag acc tcg gac acc gtg tgt<br>Gly Gln His Ala Lys Val Phe Cys Thr Lys Thr Ser Asp Thr Val Cys<br>305                       310                   315                   320 | 960 |
| gac tcc tgt gag gac agc aca tac acc cag ctc tgg aac tgg gtt ccc<br>Asp Ser Cys Glu Asp Ser Thr Tyr Thr Gln Leu Trp Asn Trp Val Pro<br>                   325                   330                   335 | 1008 |
| gag tgc ttg agc tgt ggc tcc cgc tgt agc tct gac cag gtg gaa act<br>Glu Cys Leu Ser Cys Gly Ser Arg Cys Ser Ser Asp Gln Val Glu Thr<br>             340                   345                   350 | 1056 |
| caa gcc tgc act cgg gaa cag aac cgc atc tgc acc tgc agg ccc ggc<br>Gln Ala Cys Thr Arg Glu Gln Asn Arg Ile Cys Thr Cys Arg Pro Gly<br>         355                   360                   365 | 1104 |
| tgg tac tgc gcg ctg agc aag cag gag ggg tgc cgg ctg tgc gcg ccg<br>Trp Tyr Cys Ala Leu Ser Lys Gln Glu Gly Cys Arg Leu Cys Ala Pro<br>370                       375                   380 | 1152 |
| ctg cgc aag tgc cgc ccg ggc ttc ggc gtg gcc aga cca gga act gaa<br>Leu Arg Lys Cys Arg Pro Gly Phe Gly Val Ala Arg Pro Gly Thr Glu<br>385                       390                   395                   400 | 1200 |
| aca tca gac gtg gtg tgc aag ccc tgt gcc ccg ggg acg ttc tcc aac<br>Thr Ser Asp Val Val Cys Lys Pro Cys Ala Pro Gly Thr Phe Ser Asn<br>                   405                   410                   415 | 1248 |
| acg act tca tcc acg gat att tgc agg ccc cac cag atc tgt aac gtg<br>Thr Thr Ser Ser Thr Asp Ile Cys Arg Pro His Gln Ile Cys Asn Val<br>             420                   425                   430 | 1296 |
| gtg gcc atc cct ggg aat gca agc atg gat gca gtc tgc acg tcc acg<br>Val Ala Ile Pro Gly Asn Ala Ser Met Asp Ala Val Cys Thr Ser Thr<br>         435                   440                   445 | 1344 |

-continued

```
tcc ccc acc cgg agt atg gcc cca ggg gca gta cac tta ccc cag cca      1392
Ser Pro Thr Arg Ser Met Ala Pro Gly Ala Val His Leu Pro Gln Pro
450                 455                 460 gtg tcc aca cga tcc caa cac acg cag cca act cca gaa ccc agc act      1440
Val Ser Thr Arg Ser Gln His Thr Gln Pro Thr Pro Glu Pro Ser Thr
465                 470                 475                 480 gct cca agc acc tcc ttc ctg ctc cca atg ggc ccc agc ccc cca gct      1488
Ala Pro Ser Thr Ser Phe Leu Leu Pro Met Gly Pro Ser Pro Pro Ala
                485                 490                 495 gaa ggg agc act ggc tag                                              1506
Glu Gly Ser Thr Gly *
            500
```

<210> SEQ ID NO 2
<211> LENGTH: 501
<212> TYPE: PRT
<213> ORGANISM: Artificial Sequence
<220> FEATURE:
<223> OTHER INFORMATION: Open Reading Frame of Human P75 TNF-R ECD

<400> SEQUENCE: 2

```
Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Ser Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Arg Gly Gly Gly
                245                 250                 255

Ser Gly Gly Gly Gly Ser Gly Gly Gly Ser Asp Pro Ala Gln Val
            260                 265                 270

Ala Phe Thr Pro Tyr Ala Pro Glu Pro Gly Ser Thr Cys Arg Leu Arg
```

```
                    275                 280                 285
Glu Tyr Tyr Asp Gln Thr Ala Gln Met Cys Cys Ser Lys Cys Ser Pro
    290                 295                 300
Gly Gln His Ala Lys Val Phe Cys Thr Lys Thr Ser Asp Thr Val Cys
305                 310                 315                 320
Asp Ser Cys Glu Asp Ser Thr Tyr Thr Gln Leu Trp Asn Trp Val Pro
                325                 330                 335
Glu Cys Leu Ser Cys Gly Ser Arg Cys Ser Ser Asp Gln Val Glu Thr
                340                 345                 350
Gln Ala Cys Thr Arg Glu Gln Asn Arg Ile Cys Thr Cys Arg Pro Gly
                355                 360                 365
Trp Tyr Cys Ala Leu Ser Lys Gln Glu Gly Cys Arg Leu Cys Ala Pro
            370                 375                 380
Leu Arg Lys Cys Arg Pro Gly Phe Gly Val Ala Arg Pro Gly Thr Glu
385                 390                 395                 400
Thr Ser Asp Val Val Cys Lys Pro Cys Ala Pro Gly Thr Phe Ser Asn
                405                 410                 415
Thr Thr Ser Ser Thr Asp Ile Cys Arg Pro His Gln Ile Cys Asn Val
                420                 425                 430
Val Ala Ile Pro Gly Asn Ala Ser Met Asp Ala Val Cys Thr Ser Thr
            435                 440                 445
Ser Pro Thr Arg Ser Met Ala Pro Gly Ala Val His Leu Pro Gln Pro
        450                 455                 460
Val Ser Thr Arg Ser Gln His Thr Gln Pro Thr Pro Glu Pro Ser Thr
465                 470                 475                 480
Ala Pro Ser Thr Ser Phe Leu Leu Pro Met Gly Pro Ser Pro Pro Ala
                485                 490                 495
Glu Gly Ser Thr Gly
            500

<210> SEQ ID NO 3
<211> LENGTH: 30
<212> TYPE: DNA
<213> ORGANISM: Artificial Sequence
<220> FEATURE:
<223> OTHER INFORMATION: deoxyoligonucleotide primer

<400> SEQUENCE: 3
tcggatcccg cccaggtggc atttacaccc                              30

<210> SEQ ID NO 4
<211> LENGTH: 20
<212> TYPE: DNA
<213> ORGANISM: Artificial Sequence
<220> FEATURE:
<223> OTHER INFORMATION: deoxyoligonucleotide primer

<400> SEQUENCE: 4
cggaattcta gaaggtaccc                                         20
```

SMALL MOLECULAR WEIGHT TNF RECEPTOR MULTIMERIC MOLECULE

RELATED APPLICATION(S)

This application is a Continuation of Ser. No. 08/437,533 filed May 9, 1995 now abandoned, the entire teachings of which are incorporated herein by reference.

BACKGROUND OF THE INVENTION

Tumor Necrosis Factor, a pleiotropic cytokine released by activated T cells and macrophages, is expressed as a mature 17 kDa protein that is active as a trimer (Smith, R. A. and Baglioni, C., *J. Biol. Chem.*, 262:6951 (1986). Trimeric cytokines such as Tumor Necrosis Factor (TNFα) and the closely related protein lymphotoxin (TNFβ), exert their biological activity by aggregating their cell surface receptors. The TNF trimer binds the receptors on the cell surface causing localized crosslinking of TNF receptors into clusters necessary for signal transduction.

The action of TNFα and TNFβ are mediated through two cell surface receptors, the 55 kDa (p55 TNF-R) and the 75 kDa (p75 TNF-R) receptors. Truncated forms of these receptors, comprising the extracellular domains (ECD) of the receptors, have been detected in the urine and serum as 30 kDa and 40 kDa TNF inhibitory binding proteins (Engelmann, H., et al., *J. Biol. Chem.*, 265:1531 (1990)).

TNF is a key mediator in a number of autoimmune and inflammatory diseases such as rheumatoid arthritis, septic shock, cerebral malaria and multiple sclerosis (reviewed in Tracy, K. J. and Cerami, A., *Ann. Rev. Cell. Biol.*, 9:317 (1993)). Antagonistic TNF treatment with anti-TNF antibodies and dimeric TNF-receptor-IgG fusion chimeras have shown promising therapeutic results for a variety of diseases in animal models (Lesslauer, W., et al., *Eur. J. Immunol.*, 21:2883 (1991); Kolls, J., et al., *Proc. Natl. Acad. Sci. USA*, 91:215 (1994); Baker, D., et al., *Eur. J. Immunol.*, 24:2040 (1994); Williams, R. O., et al., *Proc. Natl. Acad. Sci. USA*, 89:9784 (1993)) and human clinical trials (Elliot, M., et al., *Arthritis and Rheum.*, 36:1681 (1993)).

For example, it has been shown that the IgG-Hu p75 TNF-R ECD dimers have a 100–4000 fold higher affinity for TNF over the monomeric counterparts (Lesslauer, W., et al., *Eur. J. Immunol.*, 21:2883 (1991); Kolls, J., et al., *Proc. Natl. Acad. Sci. USA*, 91:215 (1994); Butler, D., et al., *Cytokine*, 6:616 (1994)). However, these molecules are large in size, immunogenic and include the Fc portion of the IgG which may interfere with clearance by binding to Fc receptors.

Thus, a need exists for improved TNF inhibitors which are less immunogenic and allow for faster clearance and greater tissue penetration when administered to a host.

SUMMARY OF THE INVENTION

The present invention is based on the discovery that a small molecular weight protein or tumor necrosis factor receptor (TNF-R), built from two or more TNF-R monomers linked via one or more polypeptide bridges or linkers, is active in inhibiting the biological activity of tumor necrosis factor (TNF). In one embodiment the invention relates to a receptor molecule which binds to TNF comprising all or a functional portion of the extracellular domain (ECD) of two TNF-Rs linked via a polypeptide linker. In another embodiment, the invention relates to a receptor molecule which binds to TNF comprising three TNF-Rs linked via two polypeptide linkers. The receptor molecule can include the ECDs of two or more p75 TNF-Rs or the ECDs of two or more p55 TNF-R. The receptor can further comprise a signal peptide of a secreted protein, such as the signal peptide of the extracellular domain of the TNF-R or the signal peptide of a cytokine.

In another embodiment the invention relates to isolated DNA encoding a protein or receptor molecule which binds to TNF, comprising two or more sequences encoding all or a functional portion of the ECD of TNF-Rs linked via one or more sequences encoding a polypeptide linker.

The invention further relates to a method of making a construct which expresses all or a functional portion of the ECD of two or more TNF-Rs linked via one or more polypeptide linkers comprising the steps of: a) obtaining a first vector which expresses all or a functional portion of the ECD of a first TNF-R and a signal peptide of a secreted protein; b) obtaining a second vector which expresses all or a functional portion of an ECD of a second TNF-R; and c) ligating the first vector of (a) with the second vector of (b) via a polypeptide linker. Thus, the first vector of (a) is linked to the second vector of (b) via the polypeptide linker resulting in a construct which expresses all or a functional portion of the ECD of the first TNF-R and all or a portion of the ECD of the second TNF-R linked via a polypeptide linker. The method of making a construct can further comprise one or more vectors which express a second polypeptide linker and all or a functional portion of an ECD of a third TNF-R wherein the ECD of the third TNF-R is linked to the ECD of the second TNF-R via the second polypeptide linker.

The present invention also relates to cells which express a construct which expresses all or a functional portion of the ECD of two or more TNF-Rs linked via one or more polypeptide linkers.

In another embodiment the invention relates to a method of inhibiting the biological activity of TNF in a host comprising administering to the host an effective amount of a receptor molecule which binds to TNF, the receptor comprising all or a functional portion of the ECD of two or more TNF-Rs linked via one or more polypeptide linkers. The invention can further be used in a method of treating a host for a TNF related disease comprising administering an effective amount of the receptor molecule of the present invention to a host.

The present invention also relates to protein or receptor molecules which bind cytokines that bind to receptor molecules comprising more than one subunit (e.g., IL-2 and IL-6 bind to an α or β receptor protein). The ECD of such receptors linked by a polypeptide linker have higher affinity for the cytokine, and, are effective inhibitors of the biological activity of the cytokine. Thus, the receptor comprises all or a functional portion of the ECD of two or more cytokine receptors linked via one or more polypeptide linkers. Furthermore, the receptor is less immunogenic, allows faster clearance and greater tissue penetration in the host upon administration than recombinant immunoglobulin molecules.

BRIEF DESCRIPTION OF THE FIGURES

FIG. 3 is the expected DNA sequence (SEQ ID NO: 1) and protein sequence (SEQ ID NO: 2) of the Hu p75 TNF-R ECD dimer in which the signal peptide is underlined, the polyglycine linker is boxed, and the putative N-linked glycosylation sites are indicated by a single bar.

DETAILED DESCRIPTION OF THE INVENTION

The present invention is based on the discovery of an efficient small molecular weight tumor necrosis factor/lymphotoxin antagonist which is active in inhibiting the biological activity of tumor necrosis factor (TNF). The present invention relates to a receptor molecule which binds to TNF comprising all or a functional portion of the extracellular domain (ECD) of two or more tumor necrosis factor receptors (TNF-Rs) linked via one or more polypeptide linkers. For example, the receptor molecule can comprise the ECDs of two TNF-Rs linked via a polypeptide linker to produce a dimeric TNF-R, as described in Example 1, or the ECDs of three TNF-Rs linked via two polypeptide linkers resulting in a trimeric TNF-R.

The invention also includes isolated DNA encoding a receptor which binds to TNF, comprising two or more sequences encoding all or a functional portion of the ECD of TNF-Rs linked via one or more sequences encoding a polypeptide linker. In a particular embodiment, the isolated DNA of the present invention is the sequence of FIG. 3 (SEQ ID No: 1).

As described in Example 1, in the embodiment in which the ECDs of two TNF-Rs are linked via a polypeptide linker, a small molecular weight TNF-R dimer was produced using two TNF-R monomers linked via a 15 amino acid polyglycine-serine bridge and is active in inhibiting the biological activity of TNF. As described in Example 2, this 59 kDa protein has four potential N glycosylation sites, is recognized in western blots and in the enzyme-linked immunosorbent assay with monoclonal antibodies against the p75 TNF-R.

Although the present invention is exemplified using the ECD from human p75 TNF-R, other ECDs from TNF-Rs can be used, such as the ECD from the p55 TNF-R. Also, functional fragments or portions of the ECD or derivatives thereof (including site mutations such as one or more amino acid deletions, additions and substitutions) are encompassed. The two or more ECDs can also be the same or different. Thus, the receptor molecule of the present invention is capable of binding tumor necrosis factor (TNFα) and lymphotoxin (TNFβ) and the biological activities of TNFα and TNFβ can be inhibited using the receptor molecule of the present invention.

The ECD of the TNF receptors can be derived from a suitable source for use in the present invention. For example, the ECD of the TNF-Rs can be purified from natural sources (e.g., mammalian, more particularly, human), produced by chemical synthesis or produced by recombinant DNA techniques as described in Example 1. In addition, the present invention includes nucleic acid sequences which encode the ECD of a TNF-R, as well as RNAs encoded by such nucleic acid sequences. As used herein, the ECD of the TNF-R refers to fragments and functional equivalents of the ECD of the TNF-R.

The terms "functional portion, fragment or derivative" refer to the portion of the ECD of the TNF-R protein, or the portion of the TNF-R sequence which encodes the ECD of TNF-R protein, that is of sufficient size and sequences to have the desired function (i.e., the ability to bind TNF) (PCT/GB91/01826; WO 9207076). Functional equivalents or derivatives of the ECD of TNF-R include a modified ECD of the TNF-R protein such that the resulting ECD of the TNF-R has the same or similar binding activity for TNF as the natural or endogenous TNF-R ECD, and/or nucleic acid sequences which, for example, through the degeneracy of the genetic code encode the same peptide gene product as the ECD of TNF-R and/or have the same TNF binding activity as described herein. For example, a functional equivalent of the ECD of the TNF-R can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel, F. M. et al., *Current Protocols in Molecular Biology*, Greene Publishing Assoc. and Wiley-Interscience 1989.

The polypeptide linker preferably includes suitable polypeptide linkers which link or ligate the TNF-Rs of the present invention so as to facilitate the highest binding affinity of the TNF trimer to the ECDs of the receptor molecule described herein. That is, the polypeptide linker of the present invention is of a length and composition which allows binding of the TNF trimer to the receptor of the present invention to occur to its greatest extent. Thus, preferred polypeptide linkers provide minimal steric hindrance to binding of TNF to the receptor molecule (e.g., glycine preferred), minimal immunological reaction and maximal solubility of the receptor molecule. The polypeptide linker can be from about 10 to about 30 amino acids in length, preferably between about 10 to about 20 amino acids. In one embodiment, the polypeptide linker is about 15 amino acids in length, as described in Example 1. In addition, the composition of the polypeptide linker can be for example, a polyglycine-serine linker, a polyglycine-leucine linker, polyglycine-alanine linker and a polyglycine-threonine linker.

The receptor molecule of the present invention can further comprise a signal peptide of a secreted protein to direct expression of the receptor of the present invention. A suitable signal peptide of the present invention includes the signal peptide of the ECD of the TNF-R or the signal peptide of a cytokine. Functional equivalents of the signal peptides of the present invention are also encompassed by the present invention. Functional equivalents of the signal peptide include a modified signal peptide of a secreted protein such that the resulting signal peptide has the same secretion activity as the non-modified signal peptide. Functional equivalents also include nucleic acid sequences which through the degeneracy of the genetic code encode the same signal peptide as known signal peptides of secreted proteins and have a similar secretion activity.

Thus, the order of the components of the receptor described herein can be: all or a functional portion of a first ECD of a TNF-R, a first polypeptide linker, and all or a functional portion of a second ECD of a TNF-R in one embodiment. In another embodiment the order of components can be: all or a functional portion of a first ECD of a TNF-R, a first polypeptide linker, all or a functional portion of a second ECD of a TNF-R, a second polypeptide linker, and all or a portion of a third ECD of a TNF-R. In addition, in either embodiment, the order of components can begin with a signal peptide. The receptor molecule links the components through peptide bonds and is preferably the result of a single recombinant expression unit.

The invention further relates to a method of making a construct which expresses all or a function portion of the extracellular domain of two or more TNF-Rs linked via one or more polypeptide linkers comprising the steps of: a) obtaining a first vector which expresses all or a functional portion of an ECD of a first TNF-R and a signal peptide of a secreted protein; b) obtaining a second vector which expresses all or a functional portion of an ECD of a second TNF-R; and c) ligating the vector of (a) to the vector of (b) via a polypeptide linker resulting in a construct which expresses all or a functional portion of two TNF-Rs linked via a polypeptide sequence. The method can further comprise one or more vectors which express a second polypeptide linker and all or a functional portion of a third ECD of a TNF-R wherein the third ECD of the TNF-R is linked to the second TNF-R via the second polypeptide linker.

The invention further relates to cells which express a receptor molecule which binds to tumor necrosis factor comprising all or a functional portion of the extracellular domain of two or more TNF-Rs linked via one or more polypeptide linker. Suitable cells which can be used to express the receptor molecule include yeast, bacterial and mammalian cells.

The present invention relates to receptor molecules which bind cytokines that bind to receptor molecules comprising more than one subunit. The ECD of such receptors linked by a polypeptide linker have high affinity for the cytokine, and, are effective inhibitors of the biological activity of the cytokine. Thus, the receptor comprises all or a functional portion of the ECD of two or more cytokine receptors linked via one or more polypeptide linkers employing the methods described herein. Thus, the ECD of the receptors of the present invention can be used to inhibit the biological activity of cytokines such as IL-1, IL-2, IL-6, GMCSF, IL-3 and IL-5 (Nicola, N. M. and Metcalf, D., *Cell*, 67:1–4 (1991)).

The invention further includes a method of inhibiting the biological activity of TNF comprising administering to a host an effective amount of a receptor molecule which binds TNF, the receptor comprising all or a functional portion of the ECD of two or more TNF-Rs linked via one or more polypeptide linkers. Such receptor molecules have utilities for use in research, diagnostic and/or therapeutic methods for diagnosing and/or treating animals or humans having pathologies or conditions associated with TNF. Such pathologies can include generalized or local presence of TNF or related compounds, in amounts and/or concentrations exceeding, or less than, those present in normal, healthy subject, or as related to a pathological condition.

For example, the invention includes a method of treating or preventing in a host a TNF related diseases (e.g., autoimmune diseases, inflammatory diseases bacterial, viral or parasitic infections, malignancies and/or neurodegenerative diseases) comprising administering to a host (such as a human) an effective amount of a receptor molecule which binds TNF, the receptor comprising all or a functional portion of the ECD of two or more TNF-Rs linked via one or more polypeptide linkers. For example, the method can be used to treat a host for rheumatoid arthritis, septic shock, cerebral malaria, inflammatory bowel disease, (e.g. Crohn's disease, ulcerative colitis) multiple sclerosis, allograft rejection, graft vs. host disease, neoplastic pathology (e.g., in chachexis accompanying some malignancies) and endotoxemic responses.

The receptor of the present invention can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition the receptor of the invention can be administered together with other components or biologically active agents, such as pharmaceutically acceptable surfactants (e.g., glycerides), excipients (e.g., lactose), carriers, diluents and vehicles. If desired, certain sweetening, flavoring and/or coloring agents can also be added. The receptor can be administered prophylactically or therapeutically to a host and can result in protection from amelioration of, or elimination of the TNF-related disease state.

Further the receptor molecule can be administered by in vivo expression of a polynucleotide encoding the receptor module. The "administration of protein" by definition includes the delivery of a recombinant host cell which expresses the protein in vivo. For example, the receptor molecule can be administered to a host using live vectors, wherein the live vector containing the receptor sequences are administered under conditions in which the receptor molecule is expressed in vivo. In addition, a host can be injected with a cDNA or DNA sequence, or a recombinant host cell containing the cDNA or DNA sequence, which encodes and expresses the receptor of the present invention (e.g., ex vivo infection of autologous white blood cells for delivery of protein into localized areas of the body, see e.g., U.S. Pat. No. 5,399,346, which is herein incorporated by reference).

Several expression vectors for use in making the constructs described herein and administering the receptor molecule of the present invention to a host are available commercially or can be reproduced according to recombinant DNA and cell culture techniques. For example, vector systems such as retroviral, yeast or vaccinia virus expression systems, or virus vectors can be used in the methods and compositions of the present invention (Kaufman, R. J., *J. of Method. in Cell. and Molec. Biol.*, 2:221–236 (1990)). Other techniques using naked plasmids or DNA, and cloned genes encapsidated in targets liposomes or in erythrocyte ghosts, can be used to introduce the receptor into the host (Freidman, T., *Science*, 244:1275–1281 (1990); Rabinovich, N. R., et al., *Science*, 265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molec. Cloning*, Cold Spring Harbor Press (1989); Ausubel, F. M., et al., *Current Protocols in Molecular Biology*, Greene Publishing Assoc. and Wiley-Interscience 1989)).

An "effective amount" is such that when administered, the receptor molecule of the present invention results in inhibition of the biological activity of TNF, relative to the biological activity of TNF when an effective amount of the receptor is not administered. For example, the inhibition of activity can be at least about 50%, or preferably at least about 75% at the disease site. In addition, the amount of receptor administered to a host will vary depending on a variety of factors, including the size, age, body weight, general health, sex, and diet of the host and the time of administration or particular symptoms of the TNF-related disease being treated. Adjustment and manipulation of established dosage ranges are well within the ability of those skilled in the art. In vitro and in vivo methods of determining the inhibition of TNF in a host are well known to those of skill in the art. Such in vitro assays can include a TNF cytotoxicity assay (e.g. the WEHI assay described in Example 1 or a radioimmunoassay, ELISA). In vivo methods can include rodent lethality assays and/or primate pathology model systems (Mathison et al., *J. Clin. Invest.*, 81:1925–1937 (1988); Beutler et al., *Science*, 229:869–871 (1985); Tracey et al., *Nature*, 330:662–664 (1987); Shimamoto et al., *Immunol. Lett.*, 17:311–318 (1988); Silva et al., *J. Infect. Dis.*, 162:421–427 (1990); Opal et al., *J. Infect. Dis.*, 161:1148–1152 (1990); Hinshaw et al., *Circ. Shock*, 30:279–292 (1990)).

The receptor molecule of the present invention preferably is capable of binding TNF with high affinity. That is, the binding affinity of the receptor molecules described herein for TNF approaches or is greater than the binding affinity of endogenous TNF receptors. Preferably the binding affinity of the receptor is such that the receptor binds the TNF homotrimer in a stoichiometric ratio of about 1:1.

As described in Example 3, the specific activity of the TNF/lymphotoxin inhibitor of the present invention is similar to that of a dimeric p75 TNF-R built on an Ig backbone (Butler, D., et al., *Cytokine*, 6:616 (1994)) and it is therefore capable of inhibiting TNF cytoxicity at a 1:1 molar ratio.

The receptor molecule of the present invention is expected to behave pharmacodynamically as the monomeric TNF-R and be quickly removed from the blood stream via the kidneys (Bemelmans, M. H. A., et al., *Cytokine*, 6:608 (1994); Jacobs, C. A., et al., *Intl. Rev. Exp. Pathol.* 34B:123 (1993)). However, the receptor is expected to have higher penetration to tissues than Ig fusion proteins due to its smaller molecular weight. Preferably, the molecular weight of the receptor molecule of the present invention is about 45 kd to about 130 kd. In addition, the Ig fusion proteins are expected to bind complement to the Fc receptor of a cell surface thereby facilitating development of an immune response. In contrast, the receptors of the present invention, being devoid of an Ig structure, are not expected to be immunogenic.

The invention is further illustrated in the following examples.

EXEMPLIFICATION

Example 1

Cloning of the Hu p75 TNF-R ECD Dimer

In order to express a small molecular weight Hu p75 TNF-R ECD dimer, we constructed the retroviral expression vector, Oscar, that was built in a multiple-step cloning procedure described below. Plasmids were grown using DH5α competent cells [supE44 DlacU169 f80 lacZDM15) hsdR17 recA1 endA1 gyrA96 thi-1 relA1].

PCR of Human p75 TNF-R Extracellular Domain

The Hu p75 TNF-R ECD was amplified by PCR from the pVL1393-Hu p75 TNF-R ECD plasmid using primers (1) and (2) shown below. pVL1393-Hu p75 TNF-R ECD (derived from pVL1393, In-Vitrogen) contained the Hu p75 TNF-R ECD from amino acid 1 to 205 with a 3' stop codon. The 5' primer (1) contained a BamHI restriction site. Bases 7 to 30 of primer (1) annealed to bases 70 to 93 of the mature Hu p75 TNF-R ECD. The 3' primer which anneals to the multiple cloning site of the pVL1393, downstream of the ECD insert, contained an Asp718 restriction site.

(1) 5' TCGGATCCCGCCCAGGTGGCATTTACACCC 3'(SEQ ID NO:3) 30mer (2) 5'CGGAATTCTAGAAGGTACCC 3' (SEQ ID NO:4) 20mer The reaction mix consisted of 0.02 mg pDNA, 1 mg of each primer, 0.25 mM dNTPs, 2.5 mM $MgCl_2$, 1×PCR buffer (10× buffer: 500 mM KCl, 100 mM Tris-HCl pH 8.3, 0.01% w/v gelatin) and 0.4 units of Taq DNA polymerase to a final volume of 50 μl. The amplification procedure included a denaturation step, 94° C., for 2 minutes, followed by 35 cycles of 1 minute strand separation at 94° C., 1 minute annealing at 56° C., 1 minute extension at 72° C., followed by an elongation step 10 minutes at 72° C.

Figure 1:
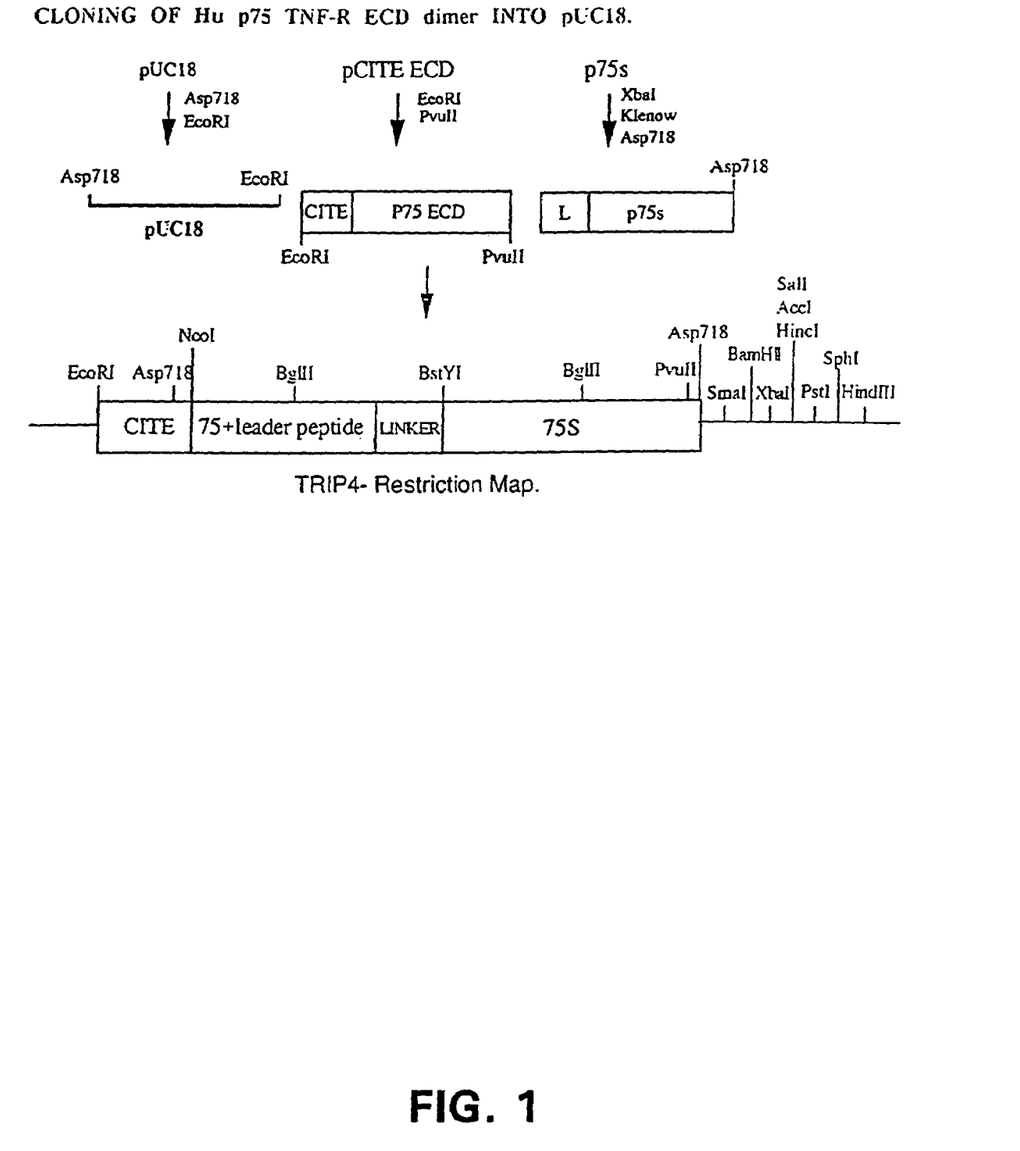
FIG. 1 is a drawing which illustrates the different stages of cloning used to obtain the Hu p75 TNF-R ECD dimer.

The extracellular domain (ECD) of the Hu p75 TNF-R ECD with its signal peptide sequence was cloned into the NcoI-XbaI sites of the vector pCITE. pCITE ECD, was derived from pCITE (Novagen) into which the Hu p75 TNF-R ECD, digested from pVL1393-Hu p75 TNF-R ECD with NcoI and XbaI, was cloned. This unit corresponds to the 5' ECD of the final dimer Hu p75 TNF-R ECD. FIG. 1 illustrates the different stages of cloning used to obtain the Hu p75 TNF-R ECD dimer. Also shown in FIG. 1 are the principal restriction enzymes sites of Hu p75 TNF-R ECD.

Cloning of the 3' Hu p75 TNF-R ECD Into pIg16

The 3' ECD was first amplified by PCR to introduce a 3' stop codon and two unique restriction sites at either end for cloning into the plasmid pIg16 which contains a single chain Fv anti-DNA antibody cloned in it. The plasmid pIg16 (Brigido, M. M., et al., *J. Immunol.*, 150:469 (1993)), derived from the pGEM-3Zf(−) vector (Promega) and containing a scFv construct was obtained from Professor David Stollar, Tufts University.

The PCR reaction product was phenol extracted, ethanol precipitated, resuspended and its ends blunted with Klenow fragment of DNA polymerase. The DNA was phenol extracted, ethanol precipitated, resuspended and digested with BamHI and Asp718. The 770 bp product was purified by agarose gel electrophoresis, reprecipitated and ligated into the BglII/Asp718 sites of pIg16.

The 3' ECD cloned into pIg16, replacing the VL domain from this construct, was named p75s. The product, p75s, was confirmed by restriction analysis and contained the Hu p75 TNF-R ECD, with a 3' stop codon, immediately downstream of the pIg16 polyglycine linker sequence (Brigido, M. M., et al., *J. Immunol.*, 150:469 (1993)).

Construction of Dimeric Hu p75 TNF-R ECD Retroviral Vector

The polyglycine-serine linker and 3' ECD were removed together from p75s and cloned into pUC18 in tandem with the 5' ECD from the pCITE-ECD construct. pUC18 was obtained from Pharmacia.

p75s was digested with XbaI, the 5' overhangs filled in with Klenow and digested with Asp718. The 800 bp fragment was purified by agarose gel electrophoresis, precipitated and resuspended in water.

pCITE ECD was digested with EcoRI and PvuII removing the Hu p75 TNF-R ECD with its signal peptide and CITE sequence. The 1500 bp fragment was purified by agarose gel electrophoresis, precipitated and resuspended in water. These two fragments were ligated into the EcoRI/Asp718 sites of pUC18 to produce the Hu p75 TNF-R ECD-dimer construct, TRIP-4, confirmed by restriction analysis.

Figure 2:
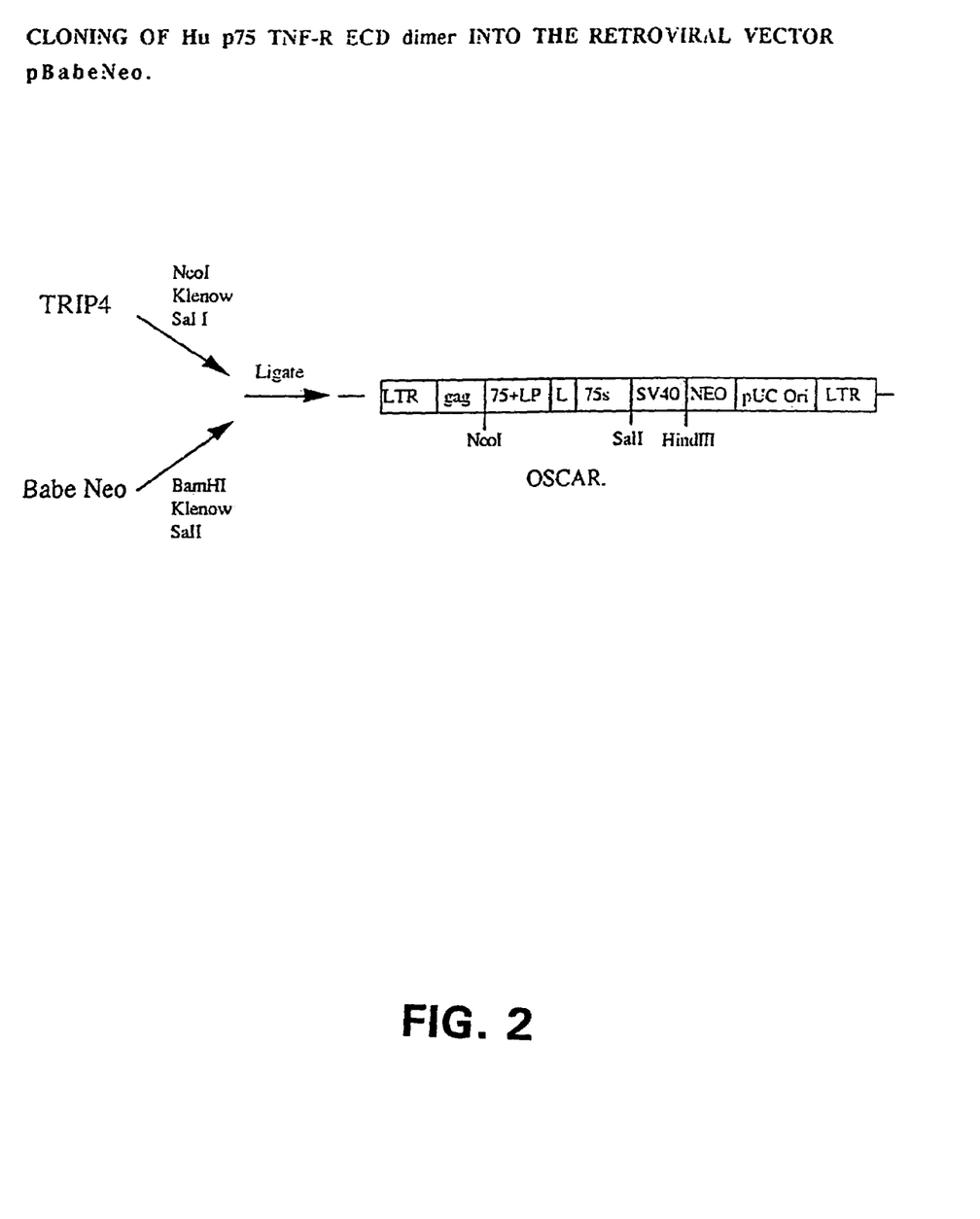
FIG. 2 is a drawing which illustrates the cloning of the Hu p75 TNF-R ECD dimer into the retroviral vector pBabe Neo used to obtain the plasmid Oscar.

The Hu p75 TNF-R ECD dimer construct was removed from the pUC18 vector and placed into the retroviral vector pBabeNeo, the clone obtained was named Oscar. TRIP-4 was digested with NcoI, the 5' overhang filled with Klenow and digested with SalI. The 1600 bp fragment was purified by agarose gel electrophoresis. The fragment was ligated into the retroviral vector pBabeNeo (Morgenstern, J. P. and Land, H., *Nucleic Acids Res.*, 18:3587 (1990)) which had been digested with BamHI, blunted with Klenow, and digested with SalI. pBabeNeo contains a MuLV LTR promoter, a neomycin resistance gene under the control of an SV40 promoter and an ampicillin gene. The Hu p75 TNF-R ECD dimer was inserted into the multiple cloning site 3' to the gag gene and 5' to the SV40 promoter (FIG. 2). The resulting clone, named Oscar, was confirmed by restriction analysis.

The open reading frame of the soluble Hu p75 TNF-R ECD dimer with its polyglycine-serine linker is shown in FIG. 3.

Example 2

Transfection of GPenvAM12 Cells with the Dimeric Hu p75 TNR-R ECD Retroviral Vector Permanent transfections were done in GPenvAM12 cells (Markowitz, D., et al., *Virology*, 167:400 (1988)). Stable transfectants expressing the Hu p75 TNF-R ECD dimer were made in the cell line GPenvAm12 and G418 was used to select for permanent transfectants. These cells constitutively express the protein which is secreted into the media.

The GPenv AM12 cells were grown and maintained in DMEM medium supplemented with 10% new-born calf serum, 2.5 units/ml penicillin, 2.5 μg/ml streptomycin and 2 mM glutamine.

For stable expression of Oscar from GPenvAM12 cells (Markowitz, D., et al., *Virology*, 167:400 (1988)), 20 μg of vector DNA were transfected into the cell line using the calcium-phosphate precipitation method. Transfected cells were selected and maintained in medium with 1 mg/ml G418. G418 resistant cell clones were pooled and tested for expression of Hu p75 TNF-R ECD dimer by ELISA, Western and inhibition of the TNF cytoxicity assay on WEHI cells.

To collect the secreted dimer from the supernatant of the stable transfected cell line, cells were grown to 80–100% confluence in the presence of 0.5 mg/ml G418. The media was removed and the cells washed twice in serum-free media. Fresh serum-free media was added to the cells, without F418, and the supernatants and cells harvested after 48 hours. Supernatants were stored at −70° C. until used.

ELISA Assay

Concentrations of Hu p75 TNF-R ECD, produced by transfected GPenvAm12 cells, were determined by ELISA. The monoclonal antibody 4C8 (Dr. Buurman, Maastricht, The Netherlands) was used as trapping antibody and the ELISA assay performed as described (Bemelmans, M. H. A., et al., *Cytokine*, 6:608 (1994)). A titration curve was prepared with a standard Hu p75 TNF-R ECD diluted 1:1 in PBS, 0.1% BSA at concentrations ranging from 62 pg/ml to 5 ng/ml. The amounts secreted averaged 560 pg/ml (3400 pg/plate) and were too low for immediate detection by Western blot analysis.

Western Blot

The serum-free medium from the GPenvAM12 cells was concentrated by centrifugation using Amicon Centricon 30 concentrators. The concentration of the soluble TNF inhibitors were determined by ELISA.

9% SDS-PAGE were run to standard western protocol and probed using the monoclonal antibody 4C8 to the Hu TNF-R75 ECD and a polyclonal anti mouse secondary antibody crosslinked with horseradish peroxidase. Westerns were developed using the ECL detection system (Amersham).

Each slot contained from left to right: 0.5 ng of dimeric Hu p75 TNF-R ECD, GPenvAM12 control supernatants 1 and 2, 1 μg soluble p75 sf2 Ig dimer (Butler, D., et al., *Cytokine*, 6:616 (1994)) and 8.7 μg soluble hs p75 TNF-R CRIP monomer. These were separated on a 9% acrylamide gel, electroblotted onto nitrocellulose, probed with 4C8 monoclonal antibodies and HRP-linked secondary antibodies and developed using the ECL system.

Figure 4:
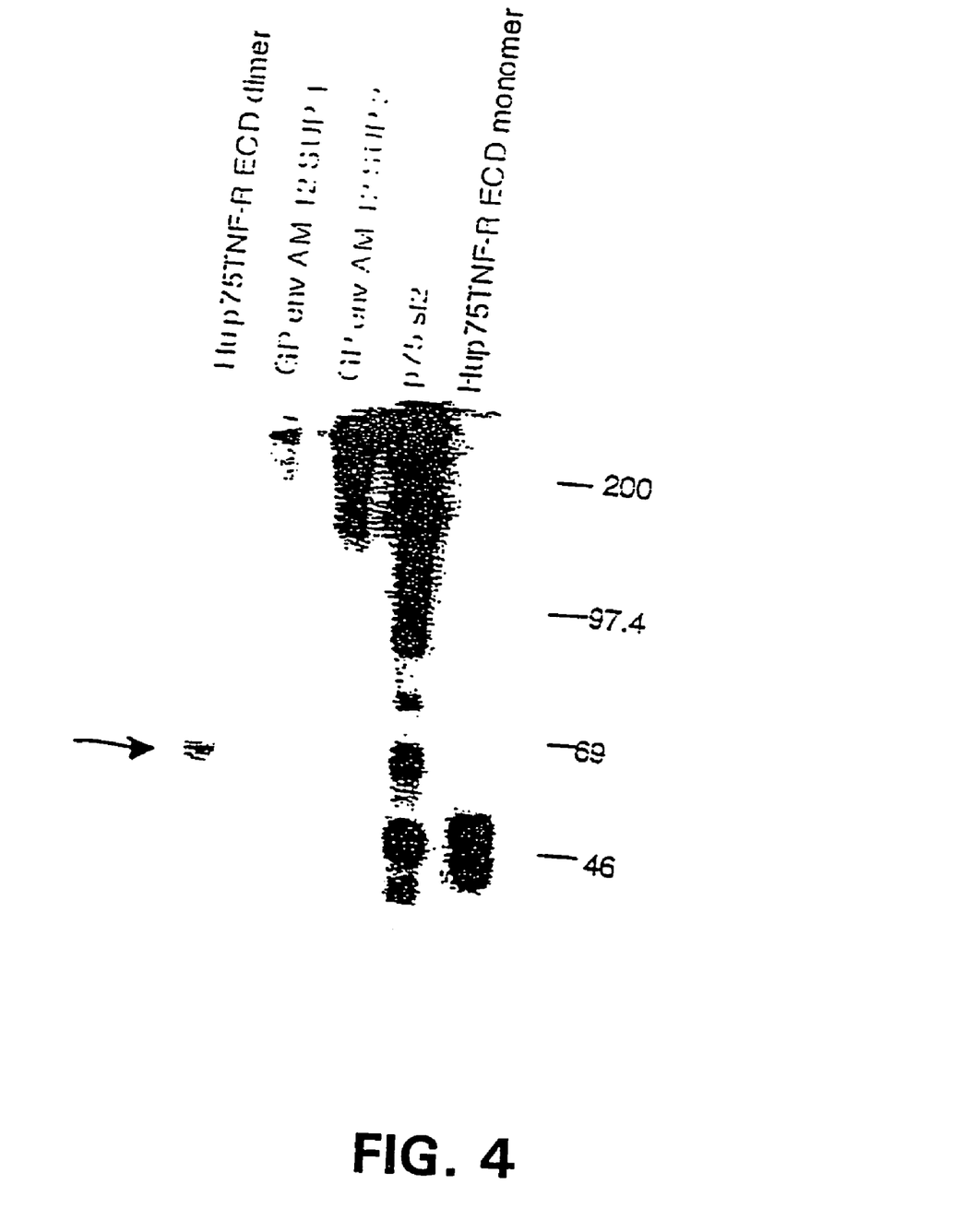
FIG. 4 is a photograph of a Western blot of the soluble Hu p75 TNF-R ECD dimer.
Figure 5A:
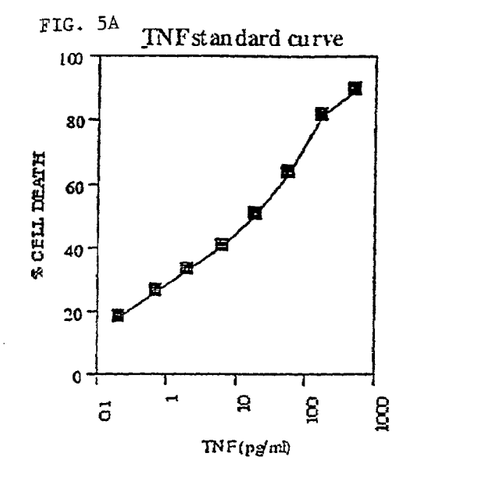
FIG. 5A is a graph of pg/ml TNF versus % cell death illustrating the standard TNF cytotoxic curve from 0.2 pg/ml to 500 pg/ml.
Figure 5B:
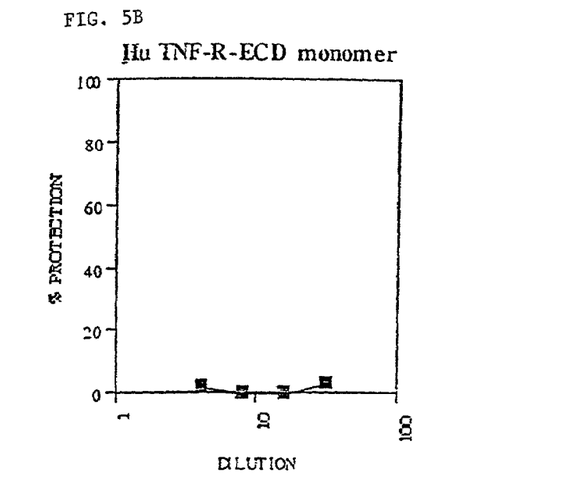
FIG. 5B is a graph of dilution versus % protection of the monomeric Hu p75 TNF-R ECD CRIP supernatant (at 3.35 ng/ml) diluted 1:4 to 1:32 incubated with 62.5 pg/ml TNF.
Figure 5C:
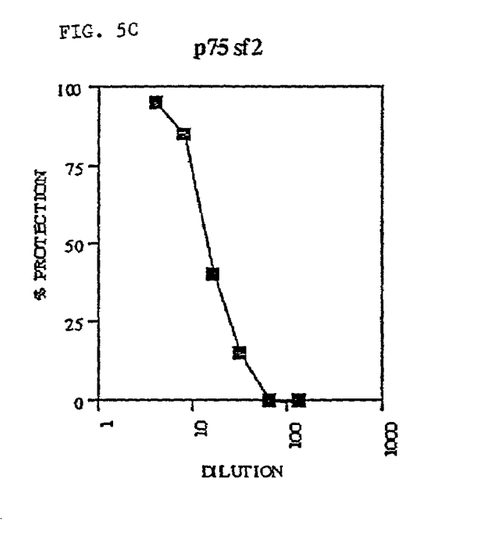
FIG. 5C is a graph of dilution versus % protection of the dimeric p75 sf2 protein (at 2.3 ng/ml) diluted 1:4 to 1:128 with 167 pg/ml human TNF.
Figure 5D:
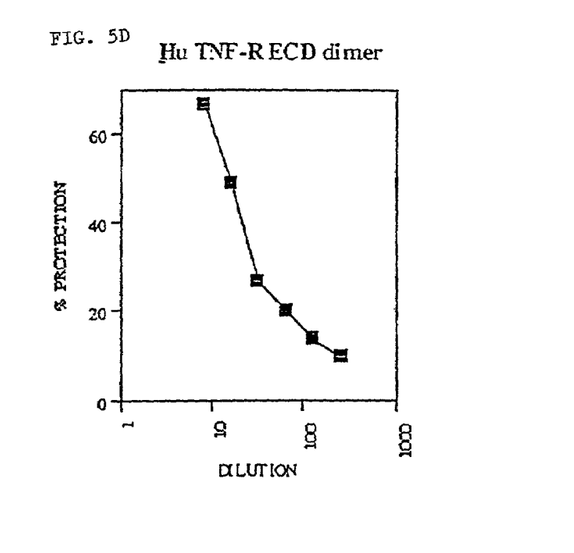
FIG. 5D is a graph of dilution versus % protection of two fold dilutions of concentrated supernatant from Oscar transfected cells (at 0.31 ng/ml) diluted from 1:4 to 1:256 incubated with 62.5 pg/ml TNF (samples were incubated for 1 hour at 37° C. and then applied in triplicate to WEHI cells as described by Butler et al., *Cytokine*, 6:616 (1994).

After concentration of the supernatants to 20 ng/ml, the Hu p75 TNF-R ECD dimer was clearly detected in the supernatant of Oscar stable tranfectants as a band of apparent molecular weight of 59 kDa (FIG. 4, left lane). The arrow indicates the sTNF-R dimer with apparent molecular weight of 59 kDa. The positions of molecular weight markers are indicated on the right. The band, detected by the monoclonal antibody 4C8 was not present in the GPenvAm12 untransfected cell supernatants. The expected molecular weight of the dimer was 53 kDa although there are four potential N-linked glycosylation sites within the Hu p75 TNF-R ECD protein (FIG. 3). This glycosylation sites may explain the increase in apparent molecular weight.

The Hu p75 TNF-R ECD dimer protein seems to be stable to proteolytic degradation since no smaller products were detected especially when compared to the Ig-fusion protein p75 sf2 (FIG. 4). The smaller difference seen between the monomeric 40 kDa (FIG. 4, right lane) and the dimeric 59 kDa dimeric Hu p75 TNF-R ECD (FIG. 4, left lane) is probably due to secondary structure obtained by the presence of the polyglycine-serine linker.

Example 3

Protection from TNF Cytotoxicity on WEHI Cells by Hu p75 TNF-R ECD Construct WEHI Assay. The concentrated supernatants were tested for protection against TNF cytotoxicity in the WEHI cell assay. To measure the inhibitory effect of the expressed Hu p75 TNF-R ECD dimer on TNF cytotoxic activity, WHEI 164 clone 13 mouse fibrosarcoma cells were used (Espevic, T., and Nissen-Meyer, J., *J. Immunol. Methods*, 95:99 (1986)).

FIG. 5 shows the protective effect obtained in this assay when TNF was preincubated with dilutions of various Hu p75 TNF-R ECD proteins. However, the two dimeric Hu p75 TNF-R ECD constructs namely p75 sf2 and Oscar efficiently protected WEHI cells from TNF cytotoxicity. Table 1 shows that 20 pg dimeric Hu TNF-R75 ECD were sufficient to inhibit by 50% the killing activity of 63.5 pg of human TNF. In comparison, 57 pg of the dimeric Hu p75 TNF-R ECD in an Ig backbone (p75 sf2) (Butler, D., et al., *Cytokine,* 6:616 (1994)) were needed to obtain the same level of protection. This lower than expected activity of the p75 sf2 construct may be due to the partial degradation in this protein (FIG. 4) that affected its efficiency. The monomeric Hu TNF-R75 ECD at 300 fold higher concentration was not effective at blocking TNF cytoxicity in the WEHI assay (FIG. 5). The cell line CRIP producing monomeric Hu p75 TNF-R ECD, was provided by Dr. Paul Robbins, University of Pittsburgh.

The concentration of 20 pg/ml Hu p75 TNF-R ECD dimer needed to inhibit by 50% the cytotoxic effect of 62.5 pg/ml TNF indicates that this antagonist is capable of binding to the TNF homotrimer in a stoichiometric ratio of almost 1:1.

TABLE 1

Specific activity of Hu p75 TNF-R ECD dimer

|  | Mr (kD) | 50% protection |
|---|---|---|
| OSCAR (Hu p75 TNF-R ECD dimer) | 59,000 | 20 pg/ml |
| hs p75 TNF-R CRIP (Hu p75 TNF-R ECD monomer) | 40,000 | N/A |
| IgG-ECD (Hu p75 TNF-R ECD dimer on Ig) | 150,000 | 57 pg/ml |

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. An isolated DNA encoding a receptor molecule which binds to tumor necrosis factor comprising two extracellular domains of tumor necrosis factor receptors linked to a polypeptide linker, wherein said polypeptide linker is covalently bonded to said extracellular domains via peptide bonds, wherein the receptor molecule is capable of binding to a tumor necrosis factor trimer in a stoichiometric ratio of almost 1:1, and wherein the DNA comprises the nucleic acid sequence set forth in SEQ ID NO:1.

2. An isolated DNA encoding a receptor molecule which binds to tumor necrosis factor comprising two extracellular domains of tumor necrosis factor receptors linked to a polypeptide linker, wherein said polypeptide linker is covalently bonded to said extracellular domains via peptide bonds, wherein the receptor molecule is capable of binding to a tumor necrosis factor trimer in a stoichiometric ratio of almost 1:1, and wherein the polypeptide comprises consecutive amino acids having the amino acid sequence set forth in SEQ ID NO:2.

3. A method of inhibiting the biological activity of tumor necrosis factor comprising administering to a subject a TNF-inhibiting amount of an isolated receptor molecule, which receptor molecule is encoded by the DNA of claim 2.

4. A method of treating a tumor necrosis factor-related disease in a subject in need thereof comprising administering to the subject a tumor necrosis factor-inhibiting amount of an isolated receptor molecule, which receptor molecule is encoded by the DNA of claim 2.

5. The method of claim 4, wherein the tumor necrosis factor-related disease is selected from the group consisting of: an autoimmune disease, and an inflammatory bowel disease.

6. The method of claim 5, wherein the tumor necrosis factor-related disease is selected from the group consisting of: rheumatoid arthritis, septic shock, cerebral malaria, inflammatory bowel disease, multiple sclerosis, and endotoxemic response.

7. The method of claim 4, wherein the tumor necrosis factor-related disease is rheumatoid arthritis.

8. A receptor molecule which binds to tumor necrosis factor comprising two extracellular domains of tumor necrosis factor receptors linked to a polypeptide linker, wherein the molecule comprises the amino acid sequence of SEQ ID NO:2.

9. A method of making a construct which expresses extracellular domains of two tumor necrosis factor receptors linked to a polypeptide linker, comprising the steps of:
    a) obtaining a first vector which expresses an extracellular domain of a first tumor necrosis factor receptor and a signal peptide of a secreted protein;
    b) obtaining a second vector which expresses an extracellular domain of a second tumor necrosis factor receptor; and
    c) ligating the first vector of (a) to the second vector of (b) using a coding sequence for a polypeptide linker so that the first vector of (a) is linked to the second vector of (b) using the coding sequence for the polypeptide linker resulting in a construct which expresses the extracellular domain of the first tumor necrosis factor receptor and the extracellular domain of the second tumor necrosis factor receptor linked using the polypeptide linker, wherein the construct expresses a receptor molecule comprising the amino acid sequence of SEQ ID NO:2.

10. An isolated cell which expresses a receptor molecule encoded by the DNA having a nucleic acid sequence comprising the nucleic acid sequence set forth in SEQ ID NO:1.

* * * * *